(12) United States Patent
Domeniconi et al.

(10) Patent No.: US 12,387,814 B2
(45) Date of Patent: Aug. 12, 2025

(54) OPTICAL FLOW BASED FORECASTING OF BINDING STATES IN MOLECULAR DYNAMIC SIMULATIONS

(71) Applicant: International Business Machines Corporation, Armonk, NY (US)

(72) Inventors: Giacomo Domeniconi, White Plains, NY (US); Leili Zhang, White Plains, NY (US); Guojing Cong, Ossining, NY (US); Chih-Chieh Yang, White Plains, NY (US); Ruhong Zhou, Fort Lee, NJ (US)

(73) Assignee: International Business Machines Corporation, Armonk, NY (US)

( * ) Notice: Subject to any disclaimer, the term of this patent is extended or adjusted under 35 U.S.C. 154(b) by 605 days.

(21) Appl. No.: 17/154,120

(22) Filed: Jan. 21, 2021

(65) Prior Publication Data

US 2022/0230702 A1     Jul. 21, 2022

(51) Int. Cl.
| | | |
|---|---|---|
| *G16B 5/20* | (2019.01) | |
| *G06F 30/27* | (2020.01) | |
| *G06F 111/08* | (2020.01) | |
| *G06T 11/00* | (2006.01) | |
| *G16B 15/30* | (2019.01) | |
| *G16B 40/00* | (2019.01) | |

(52) U.S. Cl.
CPC .............. *G16B 5/20* (2019.02); *G06F 30/27* (2020.01); *G06T 11/00* (2013.01); *G16B 15/30* (2019.02); *G16B 40/00* (2019.02); *G06F 2111/08* (2020.01); *G06T 2210/41* (2013.01)

(58) Field of Classification Search
CPC .......... G16B 5/20; G16B 15/30; G16B 40/00; G06F 30/27; G06F 2111/08; G06T 11/00; G06T 2210/41
See application file for complete search history.

(56) References Cited

U.S. PATENT DOCUMENTS

2018/0293737 A1   10/2018   Sun et al.
2018/0341754 A1   11/2018   Fan et al.

FOREIGN PATENT DOCUMENTS

CN          106709933 A      5/2017

OTHER PUBLICATIONS

Tsuchiya, Y., Taneishi, K. and Yonezawa, Y. Autoencoder-based detection of dynamic allostery triggered by ligand binding based on molecular dynamics. Journal of Chemical Information and Modeling, 59(9), pp. 4043-4051. (Year: 2019).*
Li, J., Fu, A. and Zhang, L. An overview of scoring functions used for protein-ligand interactions in molecular docking. Interdisciplinary Sciences: Computational Life Sciences, 11, pp. 320-328. (Year: 2019).*
Ragoza, M., Hochuli, J., Idrobo, E., Sunseri, J. and Koes, D.R. Protein-ligand scoring with convolutional neural networks. Journal of Chemical Information and Modeling, 57(4), pp. 942-957. (Year: 2017).*
Dashti, A., Mashayekhi, G., Shekhar, M., Ben Hail, D., Salah, S., Schwander, P., des Georges, A., Singharoy, A., Frank, J. and Ourmazd, A. Retrieving functional pathways of biomolecules from single-particle snapshots. Nature Communications, 11(1), p. 1-14. (Year: 2020).*
Jin, Q., Sorzano, C.O.S., de La Rosa-Trevin, J.M., Bilbao-Castro, J.R., Núñez-Ramírez, R., Llorca, O., Tama, F. and Jonić, S. Iterative elastic 3D-to-2D alignment method using normal modes for studying structural dynamics of large macromolecular complexes. Structure, 22(3), pp. 496-506. (Year: 2014).*
G. Cong et al. "Video Action Recognition with an Additional End-to-End Trained Temporal Stream" 2019 IEEE Winter Conference on Applications of Computer Vision (WACV), Waikoloa Village, HI pp. 51-60, 2019.
Y. Huang et al. "Efficient Parallel Inflated 3D Convolution Architecture for Action Recognition" in IEEE Access, vol. 8, pp. 45753-45765, 2020.
G. Cong et al., "Accelerating Deep Neural Network Training for Action Recognition on a Cluster of GPUs," 2018 30th International Symposium on Computer Architecture and High Performance Computing (SBAC-PAD), Lyon, France, 2018, pp. 298-305.
G. Cong, "Accelerating deep neural network training for action recognition on a cluster of GPUs High Performance Machine Learning Workshop." [Accessed Aug. 13, 2020] https://hpml2018.github.io/HPML2018_2.pdf, p. 1-22.
K. Terayama et al . . . "Machine learning accelerates MD-based binding pose prediction between ligands and proteins." Bioinformatics, 34(5), 770-778, 2018.
S.-L. Lahey, "Simulating Protein-Ligand Binding with Neural Network Potentials," ChemRxiv. Preprint, 2019. https://doi.org/10.26434/chemrxiv.11051315.v1, p. 1-7.

(Continued)

*Primary Examiner* — Olivia M. Wise
*Assistant Examiner* — Janna Nicole Schultzhaus
(74) *Attorney, Agent, or Firm* — Caleb D. Wilkes

(57) ABSTRACT

A computer-implemented method for executing a computation task in a molecular dynamic simulation includes identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms; simulating a binding state outcome of the protein structure relative to the ligand for each of the plurality of viewpoints; and predicting a probability of the protein structure binding with the ligand, based on the predicted binding state outcome for each of the plurality of viewpoints.

20 Claims, 13 Drawing Sheets

(56) References Cited

OTHER PUBLICATIONS

Decherchi et al., "The ligand binding mechanism to purine nucleoside phosphorylase elucidated via molecular dynamics and machine learning," Nature Communications, Jan. 27, 2015, 10 pages.

Doerr et al., "On-the-Fly Learning and Sampling of Ligand Binding by High-Throughput Molecular Simulations," J. Chem. Theory Comput., May 2014, http://www.qmclab.com/labwiki/files/literature/mechod/Enhanced_Sampling/Markov%20State%20Model/(2014%20jctc%20G.%20De%20Fabritiis)%20adaptive%20MSM.pdf, pp. 2064-2069.

* cited by examiner

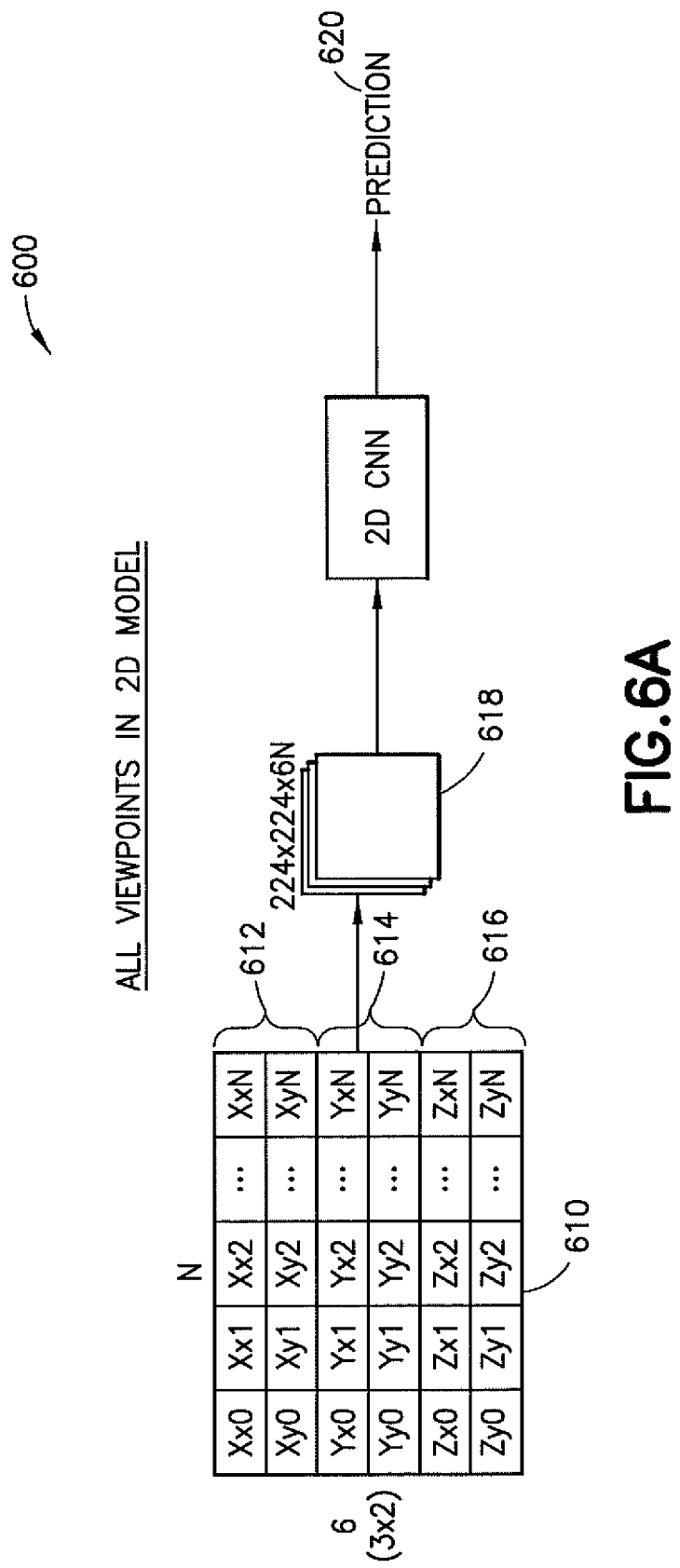

OPTICAL FLOW BASED FORECASTING OF BINDING STATES IN MOLECULAR DYNAMIC SIMULATIONS

BACKGROUND

The exemplary embodiments described herein relate generally to methods of optical simulation and, more specifically, to methods of simulation using molecular dynamics to identify stable binding states in drug-protein interactions.

Drug discovery is an $80 billion per year business. Past methodologies of drug discoveries relied heavily on experimental data, organic compound libraries, and static scoring functions. Ways to expand such data (for example, by using relatively more accurate molecular dynamic (MD) simulations) are in high demand. However, even though MD simulations may predict ligand-protein binding more accurately than traditional bioinformatics and scoring functions, it takes many GPU hours of simulations (with longer real time and more computing resources than bioinformatic methods) to obtain a potential drug candidate. It would be desirable to predict if a binding state is stable with the first few frames of a simulation to accelerate this process.

In an MD simulation, a stable binding state in a drug-protein interaction likely leads to a potential drug candidate. Each simulation usually takes hundreds of GPU hours to complete, but the majority of time is spent exploring unstable binding states. Therefore, a way to identify a stable binding state without extensive simulations is much needed because it would shorten the real time and save computing resources for discovery of new drugs. The methods as proposed herein assist researchers in saving computing time and resources, pointing out in advance the simulations that will end with undesirable outcomes.

BRIEF SUMMARY

In one exemplary aspect, a computer-implemented method for executing a computation task in a molecular dynamic simulation comprises identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

In another exemplary aspect, an apparatus comprises one or more memories having computer-readable code thereon; and one or more processors, the one or more processors, in response to retrieval and execution of the computer-readable code, causing the apparatus to perform operations comprising identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

In another exemplary aspect, a computer program product comprising a computer-readable storage medium having computer-readable program code embodied therewith is configured for identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

BRIEF DESCRIPTION OF THE SEVERAL VIEWS OF THE DRAWINGS

The foregoing and other aspects of exemplary embodiments are made more evident in the following Detailed Description, when read in conjunction with the attached Drawing Figures, wherein:

FIGS. 6A through 6E are schematic representations of 2D and 3D models that use data structures to predict binding states;

DETAILED DESCRIPTION

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

The embodiment methods described herein generally form the central part of a transferrable MD simulation engine that shortens the time for the prediction of protein-ligand interactions. Using the methods described herein, a binding state between a protein and a ligand may be predicted within about 10 nanoseconds of the start of the simulation. Uses for such methods include tastant screening, small molecule drug predictions, cancer immunotherapy, autoimmune disease immunotherapy, and the like. These methods generally involve:

identifying bonding targets and creating or constructing protein structures;
preparing MD simulation data using known ligands;
subsampling MD simulations using particular frequencies;
processing 3D models and rendering 2D images from defined viewpoints;
estimating the optical flows of the rendered 2D images;
feeding (as inputs of convolutional neural network (CNN) models) sets of optical flows and retrieving the prediction of the binding state outcome, wherein each viewpoint may provide a different prediction, then combining the different predictions to provide a final prediction; and
feeding back the simulation by increasing/decreasing the subsample frequency and continuing or stopping the MD simulation according to the prediction (or latest predictions), and further stopping the simulation if the predicted outcome is not indicated to be a binding state.

Figure 1:
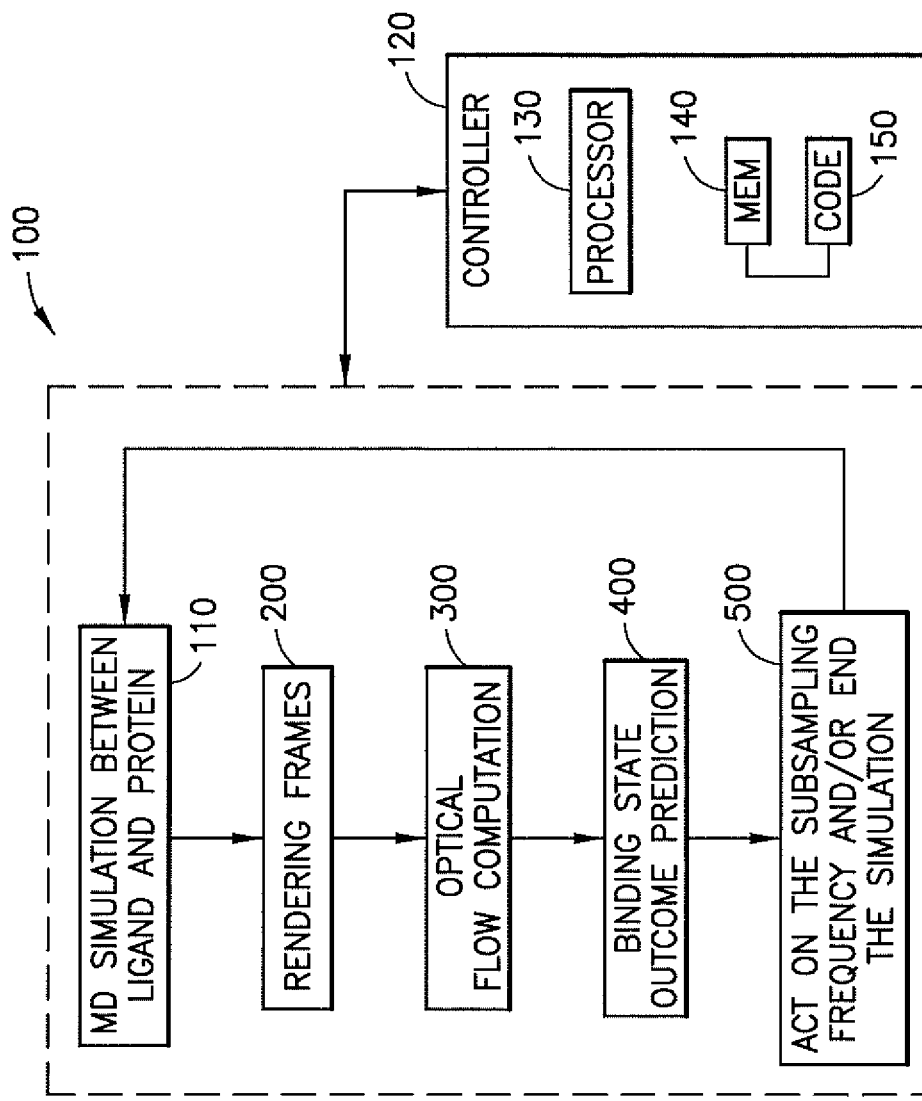
FIG. 1 is a flow diagram illustrating one example of a molecular dynamic simulation.

Referring to FIG. 1, one exemplary embodiment of an MD simulation between a ligand and a protein is shown generally at 100 and is hereinafter referred to as "simulation 100." Simulation 100 may be implemented using a computer system having a controller 120 having a processor 130 and at least one memory 140, the memory 140 having or being operable using computer readable code 150 or software embodied on any tangible medium.

The simulation 100 is accurate in predicting the protein-ligand interactions, which are directly correlated with the ligand (drug) efficacy. Stable binding states are usually the goals of protein-ligand simulations because they can be used to calculate drug binding affinities, compare drug efficacy, and improve drug efficacy. One example process of finding a stable binding state may include simulating protein-ligand binding complexes starting from a few (for example, about 10) initial states obtained from molecular docking scoring functions followed by calculating either root mean square deviations (RMSD) of the simulations or performing manual inspections (for example, carried out by an experienced scientist specialized in MD simulations). The stable binding state is then decided with the minimal RMSD or minimal movement of the ligand molecules in the protein binding pocket.

The simulation 100 is prepared in a generation step 110 in which a protein structure is created or constructed and at least one ligand is determined based on known ligands. The created or constructed protein structure and the ligand form a training set. The construction of a protein structure may be achieved, for example, by one or more of (1) using experimental methods such as X-ray crystallography to solve for a protein structure; (2) fixing the missing residues from a crystal structure, which is typically downloaded from a protein structure database; (3) using molecular modeling methods such as homology models to construct a protein structure from their homologous models; and (4) using machine learning methods to construct the protein structure using the entire protein structure database as the training set. Data pertaining to the created or constructed protein structure and the ligand are subsampled at a predetermined frequency, for example, every 100 picoseconds. A rendering step 200 is then carried out in which molecules of the protein structure are combined with the ligand to result in a rendered protein-ligand image. Control then passes to an optical flow computation step 300 and then to a binding state outcome prediction step 400. Control then passes to a feedback step 500, which alters a frequency of the subsampling and/or ends the simulation. The frequency of the subsampling may be varied in lieu of performing computations at each timestep in order to save computation time and resources. This subsampling frequency may be increased or otherwise controlled before a scheduled end of the simulation in order to magnify or observe a particular event in the simulation 100. The simulation may then be repeated.

Figure 2:
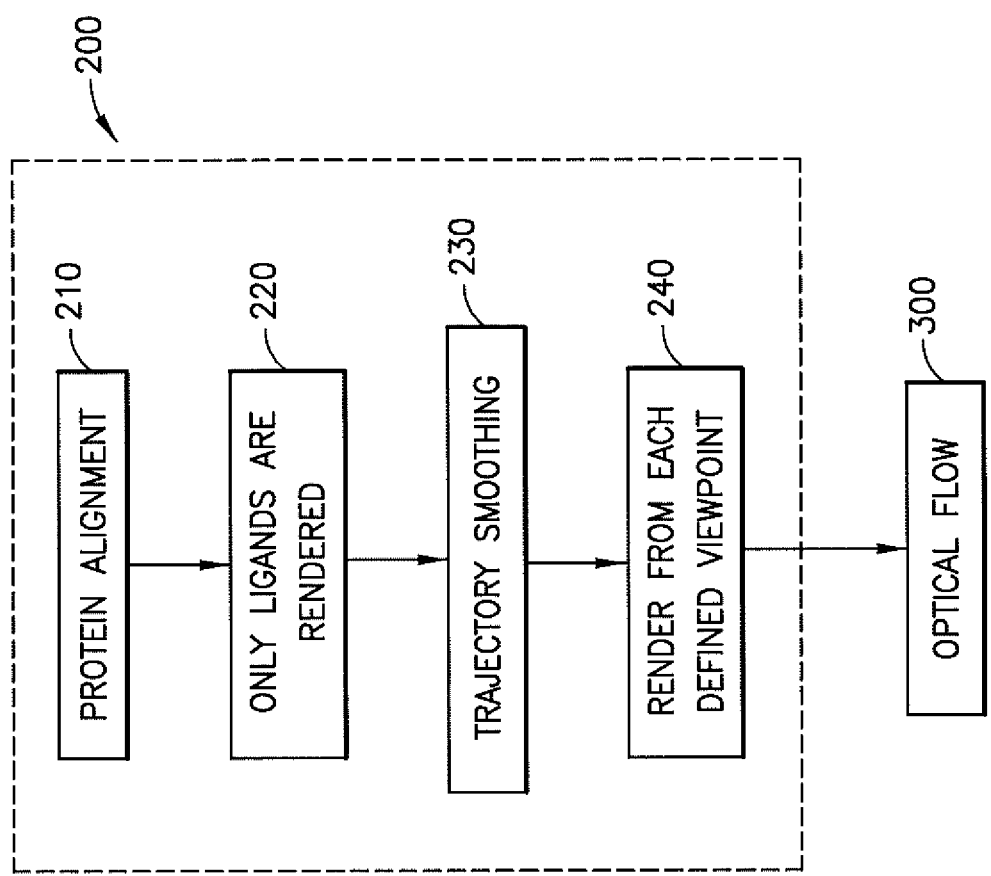
FIG. 2 is a flow diagram illustrating one example of a rendering step in the molecular dynamic simulation of FIG. 1.

Referring to FIG. 2, in the rendering step 200, the protein structures are aligned in an alignment sub-step 210, the ligands are rendered in a ligand rendering sub-step 220, trajectories are smoothed in a trajectory smoothing sub-step 230, and a final rendering sub-step 240 is carried out in which a rendering of a protein-ligand is carried out from defined viewpoints.

In the rendering step 200, to mimic the manual inspection of a MD simulation expert, a series of images of the protein-ligand molecules are processed for subsequent feeding into ML algorithms. In one example embodiment, the proteins are pre-aligned in the alignment sub-step 210 using alpha carbons as a reference. To pre-align the proteins, a transformation matrix is calculated between coordinates of alpha carbons at different time frames, and the transformation matrix is manipulated so that the root mean square displacement of the alpha carbons between any two different time frames is minimized. The transformation matrix is then applied to the coordinates of the entire system at the second of the two different time frames such that the "transformed" coordinates at the second time frame are "aligned" with coordinates of the first time frame. In this way, motion magnitudes and motion directions of the ligand molecules are commensurable. Assuming proteins are relatively rigid, the ligand molecules with spheres representing the atoms are rendered in the ligand rendering sub-step 220. The sizes of the spheres are determined by the van der Waals radius of the particular atoms. Each of the spheres corresponds to the type of the atom. When represented as a graphic on a screen, the types of atoms may be represented using colors. For example, carbon atoms may be cyan, hydrogen atoms may be white, nitrogen atoms may be blue, oxygen atoms may be red, and sulfur atoms may be yellow. The trajectory smoothing sub-step 230 results in a reduction in noise within the data, such data resulting in the final rendering sub-step 240 based on a machine learning algorithm.

Figure 3:
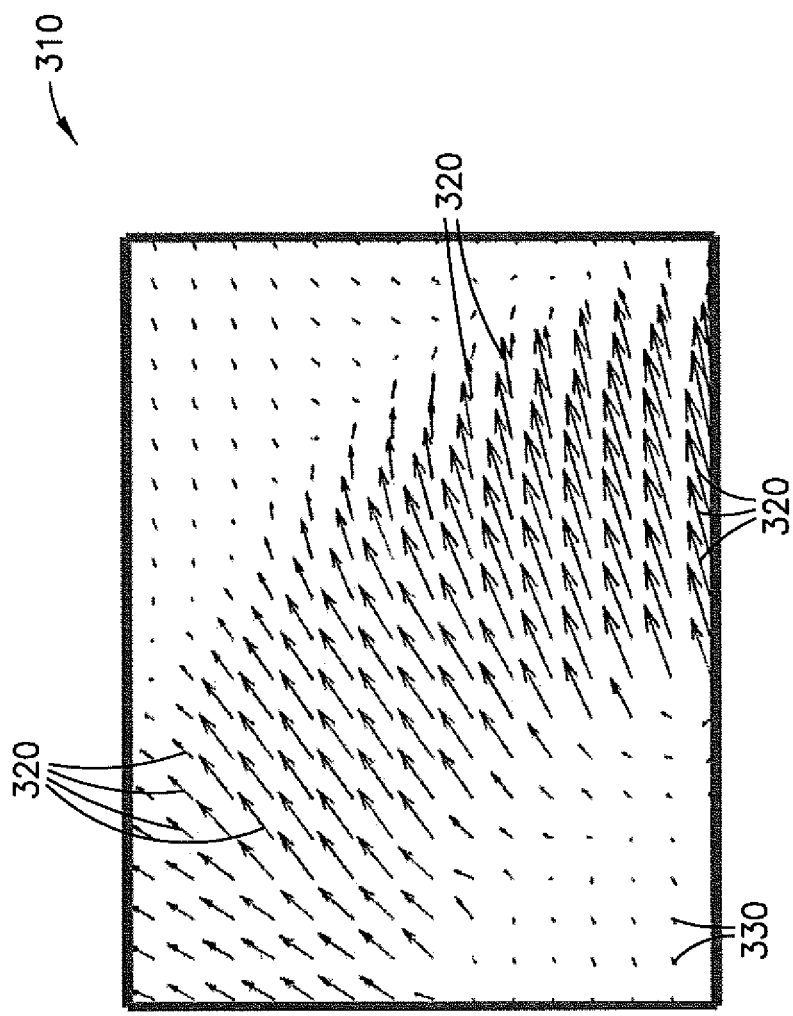
FIG. 3 is a schematic representation of one example of optical flow density in an image.

Referring now to FIG. 3, one example of dense optical flow is shown generally at 310. Optical flow refers to the visible motion of an object in an image, and the apparent "flow" of pixels in an image, as shown by arrows 320, and is the result of 3D motion being projected on a 2D image plane. As can be seen, the flow of pixels 320 increases in density from left to right. Some non-moving pixels are shown at 330. The optical flow of pixels 320 in one frame can be used as an estimation of velocity and position of objects in the next frame. One example method of optical flow estimation is TV-L1, which is based on a minimization of a function containing a data term using the L1 norm and a regularization term using the total variation of the flow, and which may be implemented in OPENCV or any other suitable platform.

Figure 4:
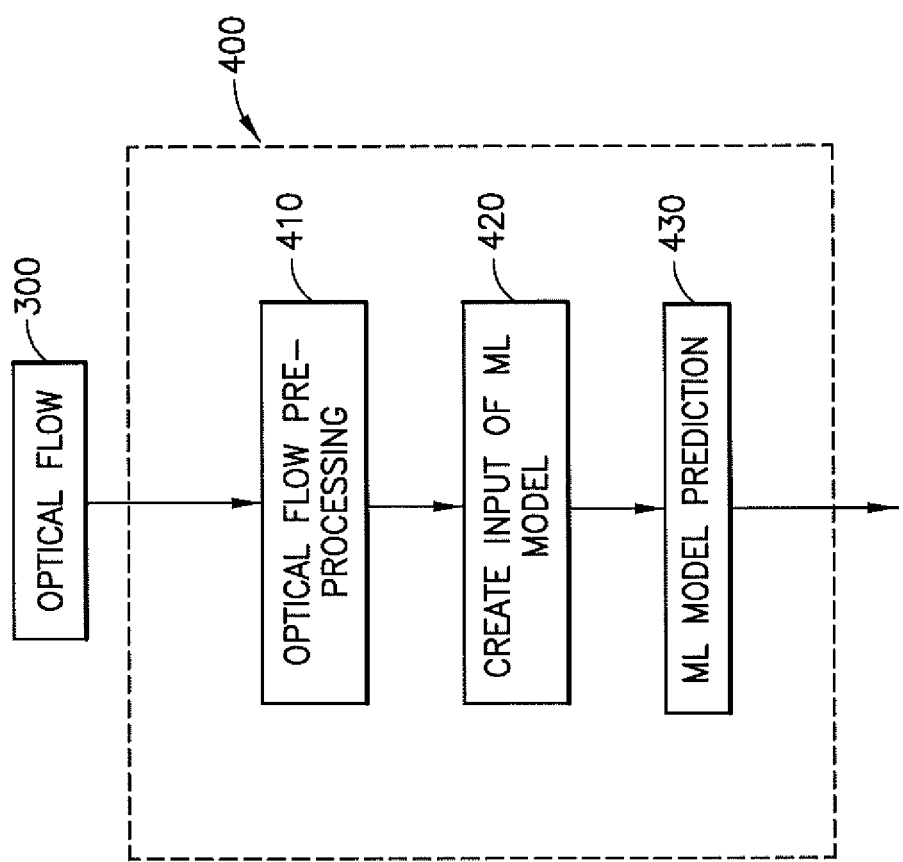
FIG. 4 is a flow diagram illustrating one example of a binding state outcome prediction step in the molecular dynamic simulation of FIG. 1.

Referring to FIG. 4, in the binding state outcome prediction step 400, the optical flow based on the rendered protein-ligand is pre-processed as shown at sub-step 410, an input of the machine learning (ML) model is created as shown at sub-step 420, and an ML model is used to analyze displacement of atoms and make a prediction, as shown at sub-step 430. Because the ML analysis is based on the displacement of atoms, the simulation 100 may be used to predict the binding outcome of ligands with novel protein structures, even novel structures not present in the training set. For example, in predicting novel structures not present in the training set, the ML analysis may be used to determine desirable bonding sites on the ligand, which can in turn be used to formulate a protein structure having corresponding structure capable of taking advantage of such bonding sites.

Figure 5:
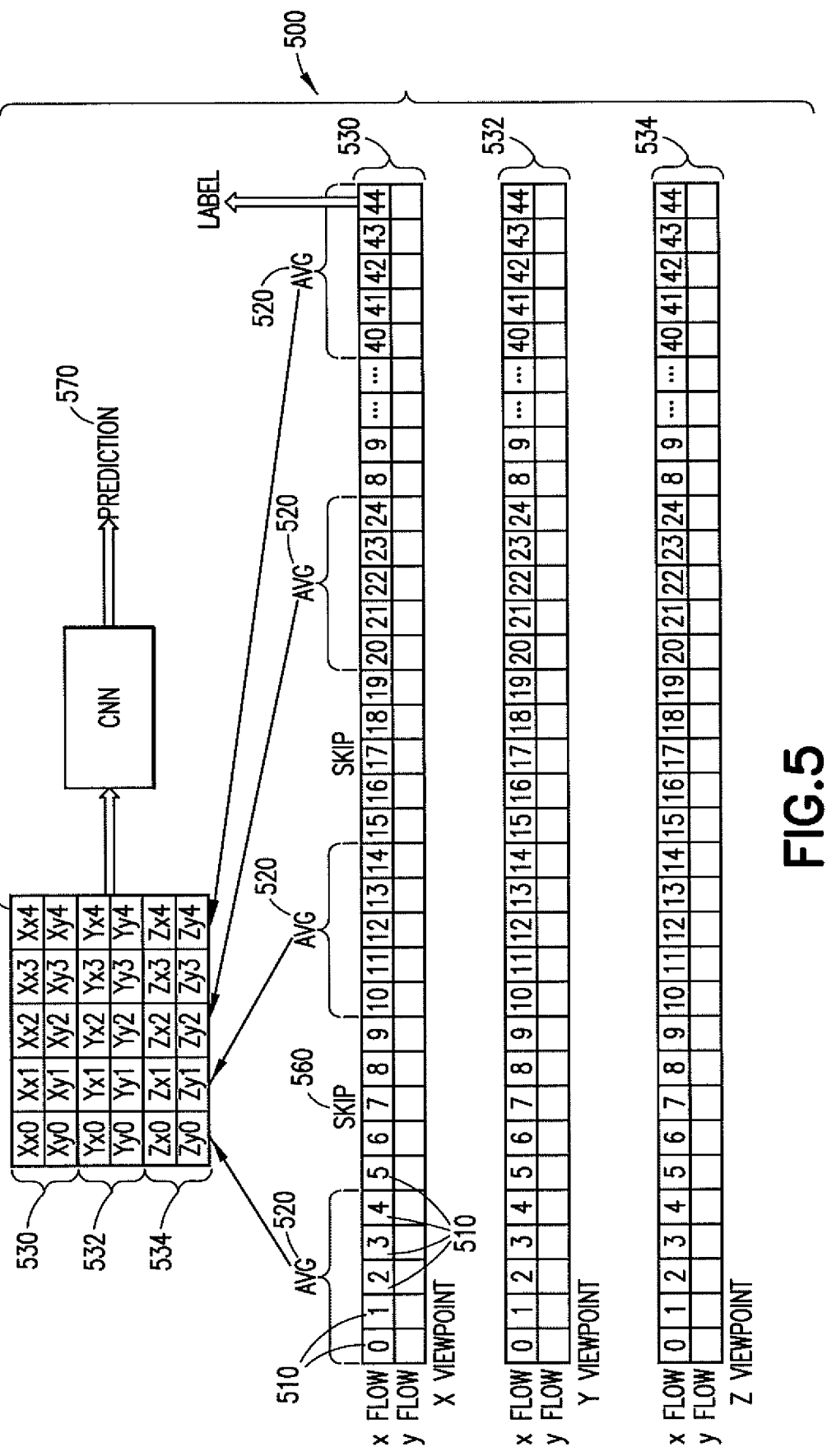
FIG. 5 is an example of a data structure used in data processing.

Referring to FIG. 5, one example of data pre-processing is shown generally at 500. In data pre-processing, different viewpoints generate different 2D rendered images. Thus, each step of a simulation may be represented with N different images, and thus N different optical flow estimations may accordingly result. As shown, an optical flow can be represented as a 2 channel image (vertical and horizontal displacement of each pixel). To reduce the high variance of the displacement, which may be generated by the typical shaking and/or displacement of the atoms in an MD simulation, the optical flows of consecutive steps 510 may be averaged, as shown at 520. It should be noted, however, that the average operation may not be useful for multiple optical flow estimations. To improve the time span represented by an input sequence, some steps may be skipped between those used in the sample.

As shown in the example of FIG. 5, there are three viewpoints, namely, X viewpoint 530, Y viewpoint 532, and Z viewpoint 534. The input 540 of the CNN is a sequence of five optical flows. Each optical flow of the input sequence is actually computed as the average 520 of five consecutive steps 510. Between each sample of the sequence, five steps are skipped (shown at 560).

In the prediction of a binding state outcome from the analysis of the atom displacement from the ML, a sequence of optical flows is fed as the input 540 to the CNN, which is trained to recognize movement patterns, in order to predict an outcome 570 of the simulation. In doing so, each viewpoint may provide a different prediction, with the different predictions being combined to provide the final prediction as the outcome 570. The different viewpoints 530, 532, and 534 may be stacked together in a single sequence, or kept separated. The CNN may be in 2D setting: input images with dimension W×H×C, with the sequence stacked together in the channels dimension. In the alternative, the CNN may be in 3D setting. In other words, the input may be a sequence of images, with dimension W×H×C×S.

Figure 6B:
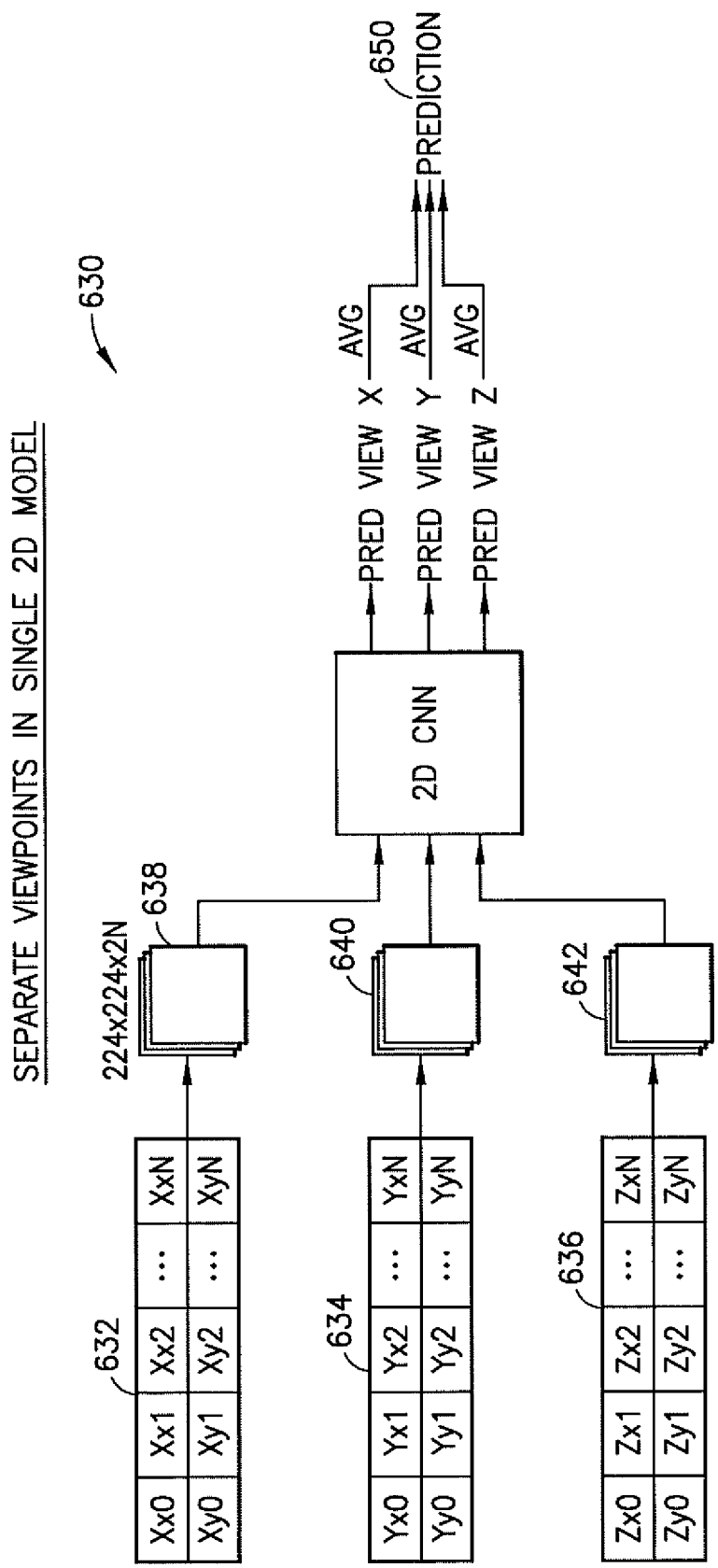

Referring to FIGS. 6A through 6E, examples of creation inputs 610 of the ML model and resulting ML model predictions are shown. In FIG. 6A, all viewpoints are shown in a 2D model 600 as 612, 614, and 616. Input 610 produces a combination predicted view 618 defined by a particular cropping size of the images from the optical flow in combination with horizontal and vertical movements for each view point (for example, 2 movements for each of 3 viewpoints (X, Y, Z)) and a length (N) of the sequence of optical flows, which is fed to the CNN. The CNN produces a final outcome prediction 620.

In FIG. 6B, separate viewpoints are shown in a single 2D model 630. The separate viewpoints are 632, 634, and 636, each of which culminate in respective combined predicted views 638, 640, and 642. This results in a predicted view in the X dimension, a predicted view in the Y dimension, and a predicted view in the Z dimension. When fed into the CNN, the predicted views 638, 640, and 642 are averaged to produce a final outcome prediction 650.

Figure 6C:
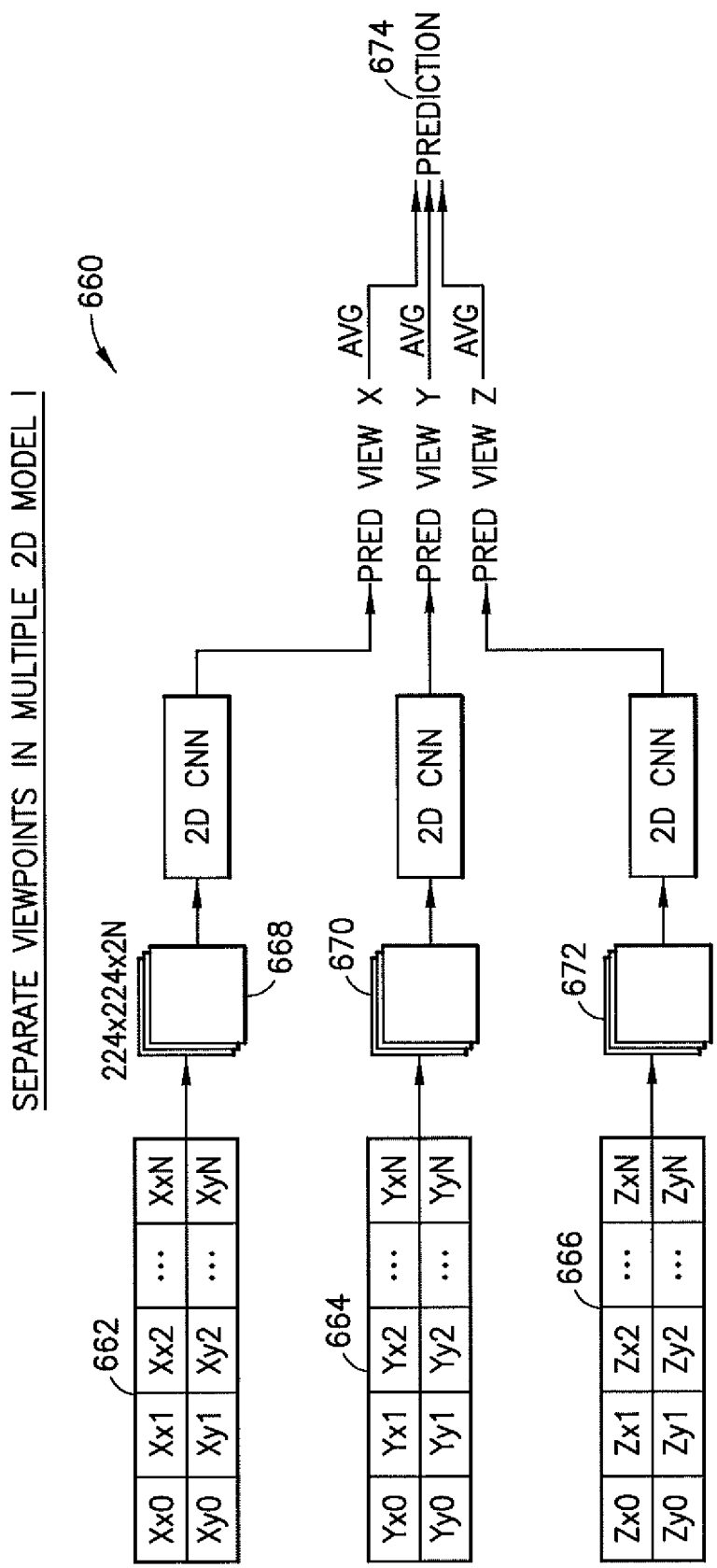

In FIG. 6C, separate viewpoints are shown in multiple 2D models to produce a single model 660, each viewpoint 662, 664, and 666 producing a predicted view 668, 670, and 672 and being fed into a respective CNN, and each being combined with the others to result in a predicted view in the X dimension, a predicted view in the Y dimension, and a predicted view in the Z dimension. Averaging the three views results in a final prediction 674.

Figure 6D:
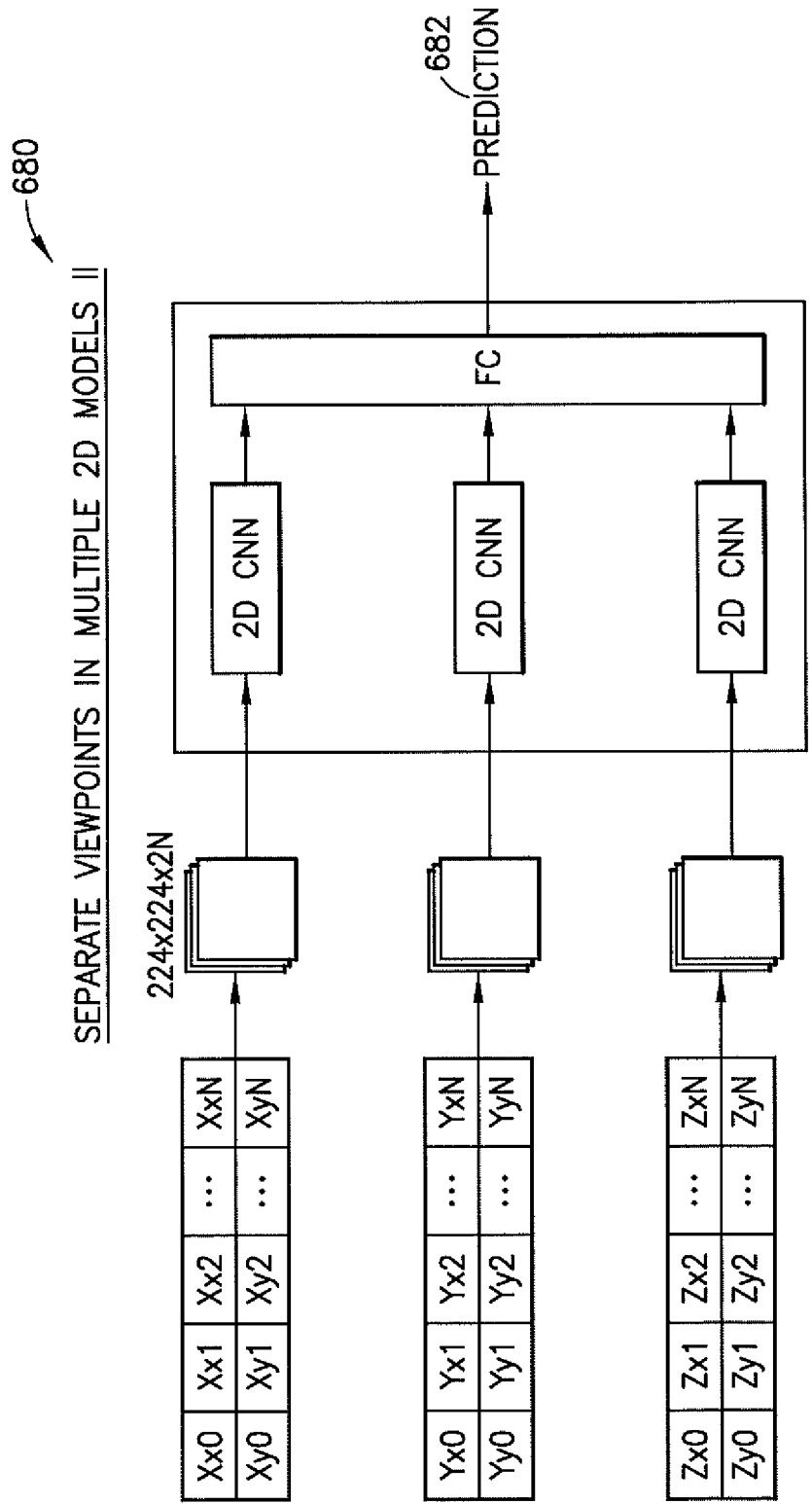

In FIG. 6D, another example of separate viewpoints (similar to those in previous Figures and not numbered here) is shown in multiple 2D models shown at 680, the output from each CNN is combined in a fully connected (FC) layer. From the FC, the final prediction 682 is reached.

Figure 6E:
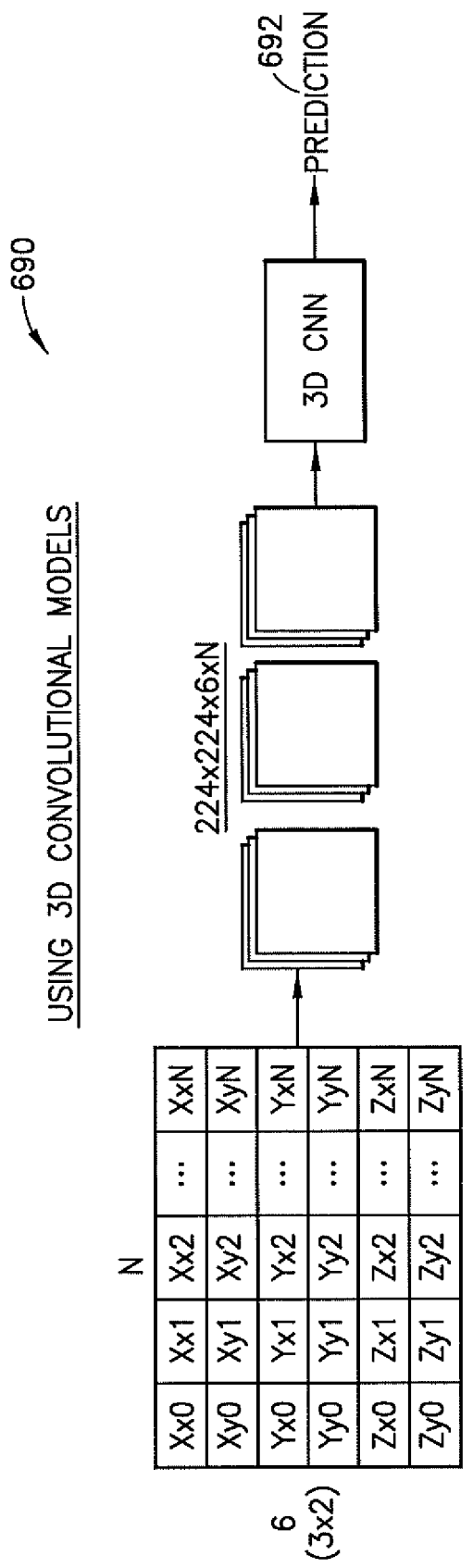

In FIG. 6E, an example using 3D convolutional models is shown at 690. From the 3D CNN, a final prediction 692 is reached. It should be noted that all of the previous settings (shown in FIGS. 6A through 6D) can also be carried out using 3D models. In doing so, there would be a fourth dimension in the data representing the sequence of N frames.

As shown in the Table below, the results with the setting "all viewpoints in a 2D model" are shown. Training/test sets are respectively 71 and 10 simulations, from 15 different ligand structures. Each simulation is subsampled with a ratio of 1/50. The results illustrate an accuracy of 0.8317.

TABLE

Results achieved with 2D models

|  | Precision | Recall | F1 |
| --- | --- | --- | --- |
| Non-binding | 0.8990 | 0.6673 | 0.7660 |
| Binding | 0.8020 | 0.9473 | 0.8686 |
| Average | 0.8420 | 0.8317 | 0.8262 |

Figure 7:
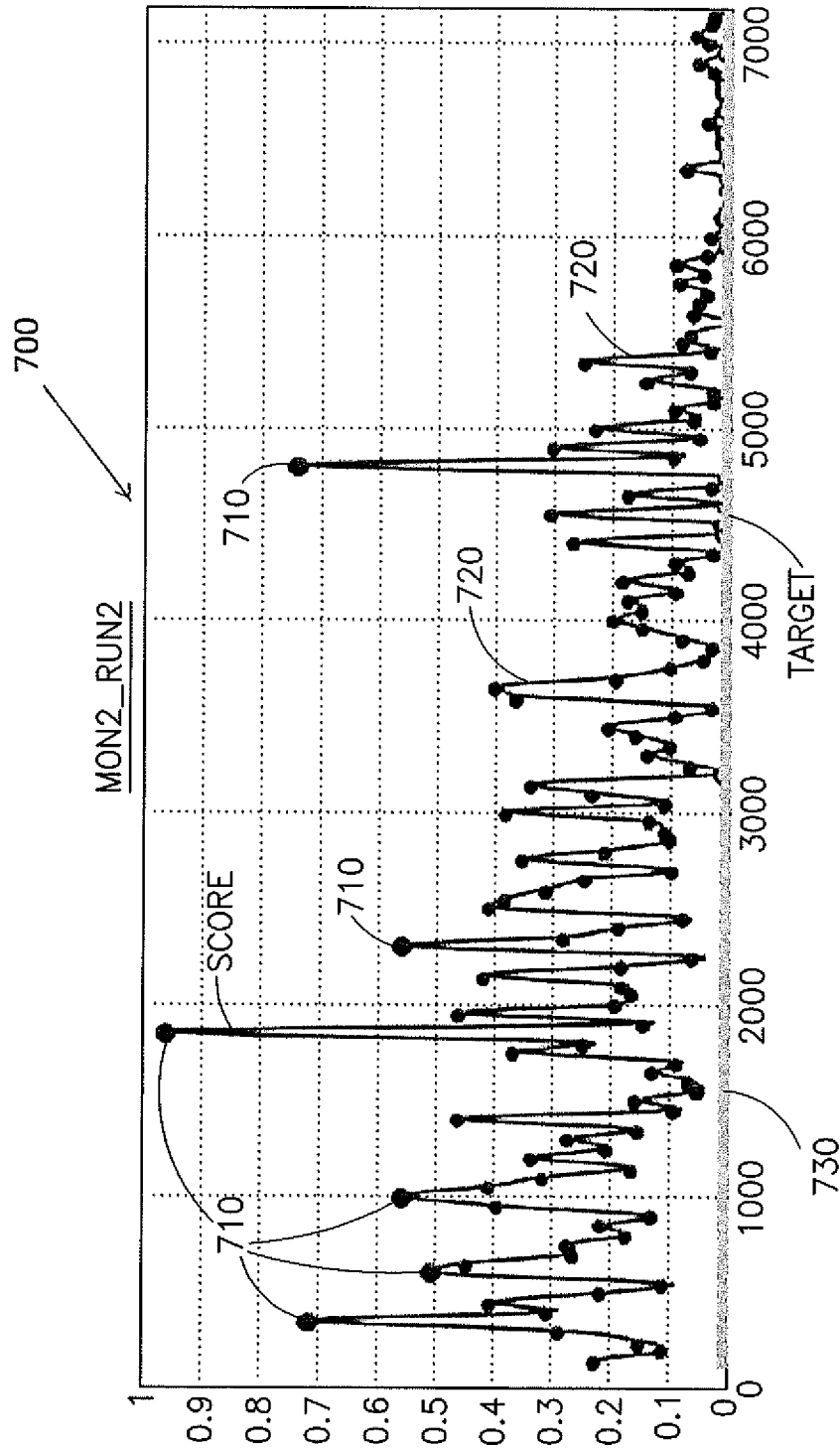
FIG. 7 is a graphical representation of one example of a simulation.

Referring to FIG. 7, a graphical representation of one example of a simulation between a sweetener (monatin) and a binding domain of a sweet taste receptor (T1R2) that did not result in a binding state is depicted at 700. In the graph 700, the model is able to predict in advance the non-binding outcome with a few frames erroneously predicted at points 710. The score values are shown at 720, and the target values are at 730.

Figure 8:
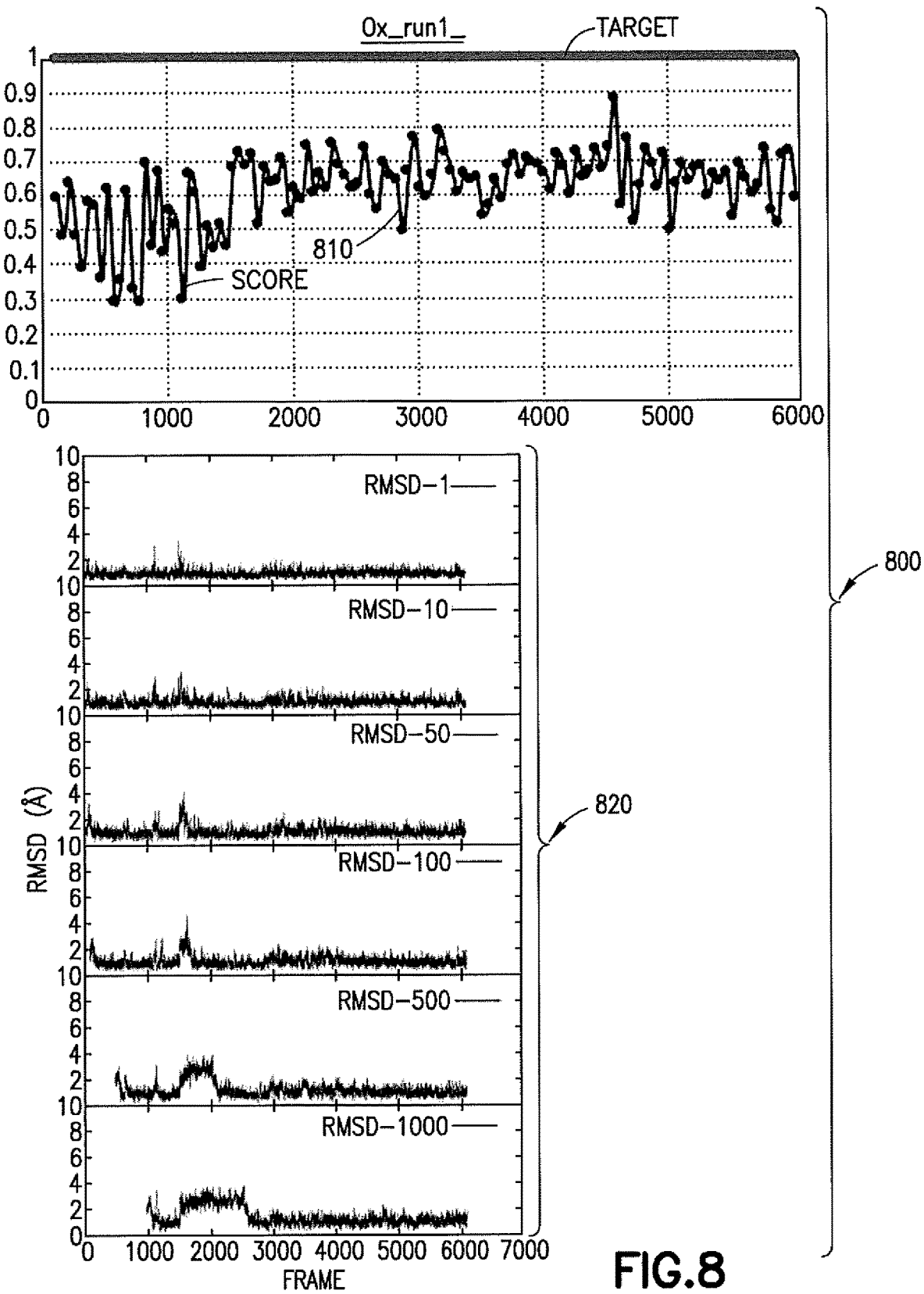
FIG. 8 is a graphical representation of one example of a simulation resulting in a binding state.
Figure 9:
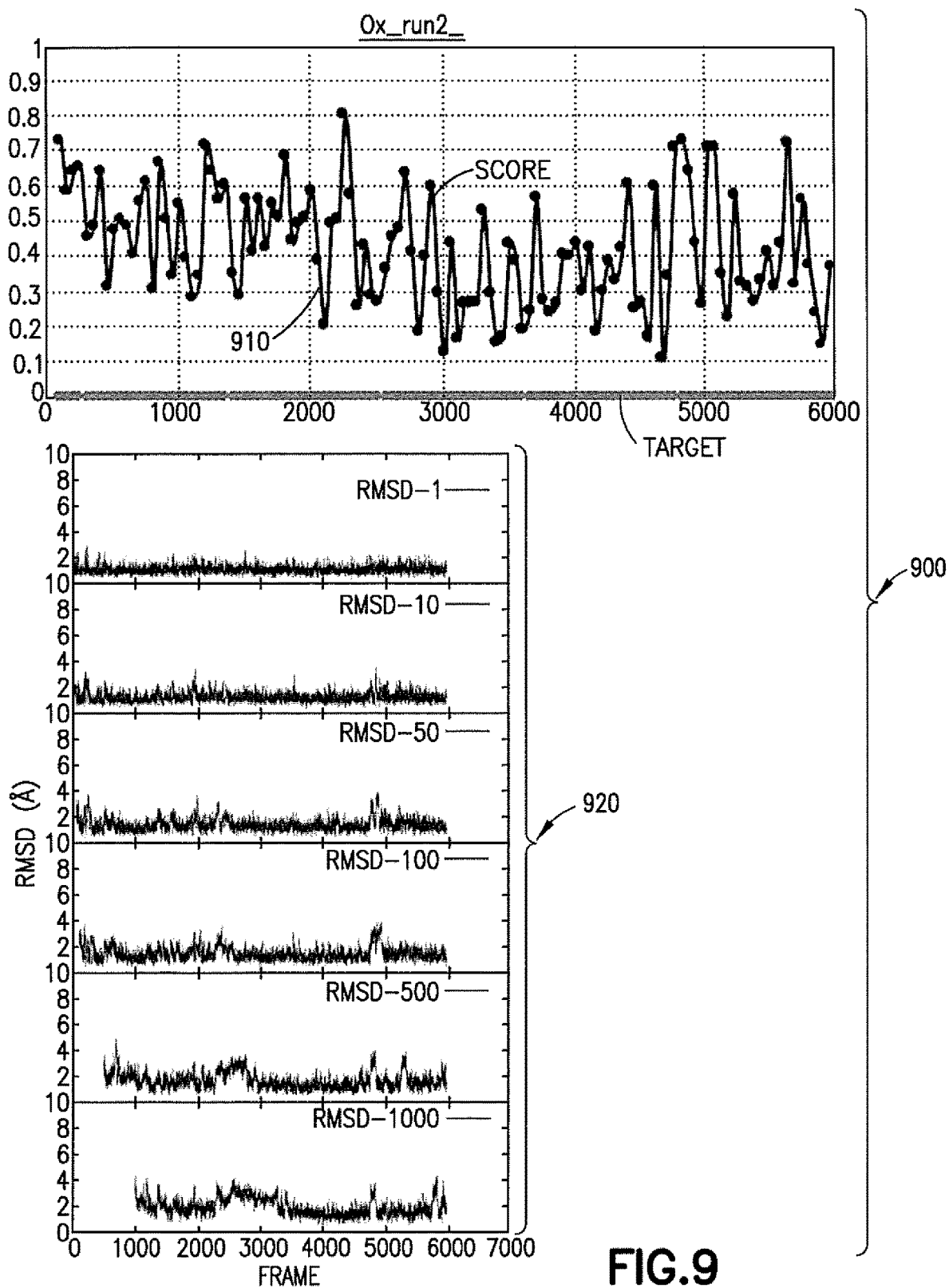
FIG. 9 is a graphical representation of one example of a simulation not resulting in a binding state.

Referring to FIGS. 8 and 9, graphical illustrations of two simulations are shown at 800 and 900, respectively. Here, a sweetener (OX) is present only in a test set with the two simulations. The ligand structure is completely new to the prediction model. In both FIG. 8 and FIG. 9, the predictions of the model shown by line 810 and 910 provide a good perspective of outcomes of each simulation, which is notable by the RMSD 820 and 920.

Referring now to all the Figures, in one example, a computer-implemented method comprises: identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

The method may further comprise feeding back the predicted probability of the protein structure binding with the ligand to the step of computing optical flows by altering a rate at which the data pertaining to the constructed protein structure and the image of the known ligand at a particular frequency is subsampled. In simulating the binding state outcome for each of the plurality of viewpoints, the plurality of viewpoints may provide at least two different predictions. Rendering the image of the ligand may comprise selecting the ligand from a set of known ligands. Computing optical flows of the protein structure relative to the ligand may comprise defining a first position of the protein structure relative to the ligand in a first image, defining a second position of the protein structure relative to the ligand in a second image, and estimating a third position of the protein structure relative to the ligand. The rendered two-dimensional image of the protein structure relative to the ligand may correspond to frames of the molecular dynamic simulation. The machine learning may be independent of the structure of the ligand. The machine learning may comprise using a neural network. The machine learning using the neural network may comprise processing to create a sequence of the optical flows that are fed as an input to the neural network.

In another example, an apparatus comprises one or more memories having computer-readable code thereon; and one or more processors, the one or more processors, in response to retrieval and execution of the computer-readable code, causing the apparatus to perform operations comprising identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

The apparatus may be further caused to feed back the predicted probability of the protein structure binding with the ligand to the computing of optical flows by altering a rate at which the data pertaining to the constructed protein structure and the image of the known ligand at a particular frequency is subsampled. In causing the apparatus to simulate the binding state outcome for each of the plurality of viewpoints, the plurality of viewpoints may provide at least two different predictions. The rendered two-dimensional image of the protein structure relative to the ligand may correspond to frames of the molecular dynamic simulation. The machine learning may be independent of the structure of the ligand and may comprise using a neural network.

In another example, a computer program product comprises: a computer program product comprising a computer-readable storage medium having computer-readable program code embodied therewith is configured for identifying a bonding target on a ligand; constructing a protein structure; rendering an image of the ligand; subsampling data pertaining to the constructed protein structure and the image of the ligand at a particular frequency; rendering a two-dimensional image of the constructed protein structure relative to the ligand from a plurality of viewpoints; computing optical flows of the protein structure relative to the ligand based on the two-dimensional image; analyzing the optical flows to determine a displacement of atoms of the protein structure relative to the ligand, the analyzing of the optical flows comprising processing data from the optical flows using machine learning to predict one or more movements of the atoms; simulating a binding state outcome of the protein structure relative to the ligand for each of the plurality of viewpoints; and predicting a probability of the protein structure binding with the ligand, based on the predicted binding state outcome for each of the plurality of viewpoints.

The computer program product may be further configured for feeding back the predicted probability of the protein structure binding with the ligand to the computing of optical flows by altering a rate at which the data pertaining to the constructed protein structure and the image of the known ligand at a particular frequency is subsampled. The machine learning may be independent of the structure of the ligand. The machine learning may comprise using a neural network. The machine learning using the neural network may comprise processing to create a sequence of the optical flows that are fed as an input to the neural network.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In the foregoing description, numerous specific details are set forth, such as particular structures, components, materials, dimensions, processing steps, and techniques, in order to provide a thorough understanding of the exemplary embodiments disclosed herein. However, it will be appreciated by one of ordinary skill of the art that the exemplary embodiments disclosed herein may be practiced without these specific details. Additionally, details of well-known structures or processing steps may have been omitted or may have not been described in order to avoid obscuring the presented embodiments.

The description of the present invention has been presented for purposes of illustration and description, but is not intended to be exhaustive or limiting in the form disclosed. Many modifications and variations will be apparent to those of ordinary skill in the art without departing from the scope of the invention. The embodiments were chosen and described in order to best explain the principles of the invention and the practical applications, and to enable others of ordinary skill in the art to understand the invention for various embodiments with various modifications as are suited to the particular uses contemplated.

What is claimed is:

1. A computer implemented method comprising:
rendering, via a computer, digital two-dimensional images of a protein structure relative to a ligand from multiple viewpoints of the protein structure and the ligand, wherein the digital two-dimensional images are rendered in one or more sequences;
determining, via the computer using computer vision artificial intelligence, optical flows of the protein structure relative to the ligand based on the digital two-dimensional images and the one or more sequences; and analyzing the optical flows to determine a displacement of atoms of the protein structure relative to the ligand, the analyzing of the optical flows comprising processing data from the optical flows using machine learning to predict atom movements, each predicted atom movement corresponding to one of the multiple viewpoints, wherein the machine learning further predicts a binding state outcome of the protein structure relative to the ligand for each of the multiple viewpoints based on the predicted atom movements, and wherein the machine learning further predicts a probability of the protein structure binding with the ligand based on the predicted binding state outcome for each of the multiple viewpoints, and wherein the machine learning implements a convolutional neural network for the predictions.

2. The method of claim 1, further comprising feeding back the predicted probability of the protein structure binding with the ligand to a previous step of the method by altering a rate at which data pertaining to the protein structure and the ligand at a particular frequency is subsampled.

3. The method of claim 1, wherein in predicting the probability of the protein structure binding with the ligand, at least two different predictions from respective viewpoints are combined.

4. The method of claim 1, wherein the rendering the digital two-dimensional images of the protein structure relative to the ligand comprises selecting the ligand from a set of known ligands.

5. The method of claim 1, wherein the determining the optical flows of the protein structure relative to the ligand comprises defining a first position of the protein structure relative to the ligand in a first image of the rendered digital two-dimensional image, defining a second position of the protein structure relative to the ligand in a second image of the rendered digital two-dimensional image, and estimating a third position of the protein structure relative to the ligand based on the first position and the second position.

6. The method of claim 1, wherein the rendered digital two-dimensional images of the protein structure relative to the ligand correspond to respective time frames of a molecular dynamic simulation.

7. The method of claim 1, wherein the machine learning is independent of the structure of the ligand.

8. The method of claim 1, wherein the one or more sequences comprise steps and one or more skips in the steps.

9. The method of claim 1, wherein inputs to the machine learning are averages of consecutive steps of the optical flows.

10. The method of claim 1, wherein the rendering comprises pre-aligning, via the computer, the protein structures using alpha carbons as references.

11. The method of claim 1, wherein the rendering comprises pre-aligning, via the computer, the protein structures using a transformation matrix applied to coordinates of elements of the protein structures.

12. The method of claim 1, further comprising performing a molecular dynamic simulation that includes repeating the rendering, the determining of the optical flows, and the analyzing of the optical flows, and wherein the molecular dynamic simulation further comprises:

evaluating, based on the predicted binding state outcome, continuance of the molecular dynamic simulation, wherein the evaluating includes ending the molecular dynamic simulation in response to the predicted binding state outcome including a prediction of a stable binding state.

13. The method of claim 1, further comprising producing a substance which incorporates the protein structure, in response to the probability indicating a stable binding state.

14. The method of claim 1, wherein the optical flows are two-channel optical flows.

15. The method of claim 14, wherein the two-channel optical flows are based on a first channel for vertical displacement and a second channel for horizontal displacement of each pixel.

16. The method of claim 1, further comprising using machine learning with a protein structure database as a training set to produce the protein structure for the rendering.

17. An apparatus comprising:
one or more memories having computer-readable code thereon; and
one or more processors, wherein the one or more processors, in response to retrieval and execution of the computer-readable code, cause the apparatus to perform operations comprising:
rendering digital two-dimensional images of a protein structure relative to a ligand from multiple viewpoints of the protein structure and the ligand, wherein the digital two-dimensional images are rendered in one or more sequences;
determining, using computer vision artificial intelligence, optical flows of the protein structure relative to the ligand based on the digital two-dimensional images and the one or more sequences; and
analyzing the optical flows to determine a displacement of atoms of the protein structure relative to the ligand, the analyzing of the optical flows comprising processing data from the optical flows using machine learning to predict atom movements, each predicted atom movement corresponding to one of the multiple viewpoints, wherein the machine learning further predicts a binding state outcome of the protein structure relative to the ligand for each of the multiple viewpoints based on the predicted atom movements, wherein the machine learning further predicts a probability of the protein structure binding with the ligand, based on the predicted binding state outcome for each of the multiple viewpoints, and wherein the machine learning implements a convolutional neural network for the predictions.

18. A computer program product comprising: a computer-readable storage medium having computer-readable program code embodied therewith, the computer-readable program code executable to cause a computer system to perform:
rendering digital two-dimensional images of a protein structure relative to a ligand from multiple viewpoints of the protein structure and the ligand, wherein the digital two-dimensional images are rendered in one or more sequences;
determining, via computer vision artificial intelligence, optical flows of the protein structure relative to the ligand based on the digital two-dimensional images and based on the one or more sequences; and
analyzing the optical flows to determine a displacement of atoms of the protein structure relative to the ligand, the analyzing of the optical flows comprising processing data from the optical flows using machine learning to predict atom movements, each predicted atom movement corresponding to one of the multiple viewpoints, wherein the machine learning further predicts a binding state outcome of the protein structure relative to the ligand for each of the multiple viewpoints based on the predicted atom movements, wherein the machine learning further predicts a probability of the protein structure binding with the ligand, based on the predicted binding state outcome for each of the multiple viewpoints, and wherein the machine learning implements a convolutional neural network for the predictions.

19. The computer program product of claim 18, wherein the computer-readable program code further causes the computer system to feed back the predicted probability of the protein structure binding with the ligand to a previous step performed by the computer system executing the computer-readable program code by altering a rate at which data pertaining to the protein structure and the ligand at a particular frequency is subsampled.

20. The computer program product of claim 18, wherein in predicting the probability of the protein structure binding with the ligand, at least two different predictions from respective viewpoints are combined.

\* \* \* \* \*